United States Patent
Johnson et al.

(10) Patent No.: US 6,756,519 B2
(45) Date of Patent: Jun. 29, 2004

(54) SEGMENTED PRODUCT WITH DISPENSING TABS

(75) Inventors: Chris Johnson, Huntington Beach, CA (US); Drew O'Connell, Coldspring Harbor, NY (US)

(73) Assignee: Cirrus Healthcare Products, LLC, Coldspring Harbor, NY (US)

( * ) Notice: Subject to any disclaimer, the term of this patent is extended or adjusted under 35 U.S.C. 154(b) by 206 days.

(21) Appl. No.: 10/057,421

(22) Filed: Jan. 25, 2002

(65) Prior Publication Data

US 2003/0204158 A1 Oct. 30, 2003

(51) Int. Cl.[7] .......................... A61F 13/00; B65D 85/66; A61B 17/06
(52) U.S. Cl. ............................ 602/58; 602/42; 602/52; 602/57; 206/401; 206/440
(58) Field of Search ............................ 602/41, 42, 54, 602/57, 58, 59; 206/440, 441, 389, 391, 393, 394, 396, 400, 401, 55, 413, 404, 411, 412

(56) References Cited

U.S. PATENT DOCUMENTS

| | | |
|---|---|---|
| 3,530,494 A | 9/1970 | Baratta |
| 4,512,462 A | 4/1985 | Dills |
| 4,727,616 A | 3/1988 | Kucera et al. |
| 4,807,753 A | 2/1989 | Goldstein |
| 5,782,786 A | 7/1998 | Tomaiuolo |
| 6,014,788 A | 1/2000 | Jaffri |
| 6,213,343 B1 | 4/2001 | Damikolas |

Primary Examiner—Kim M. Lewis
(74) Attorney, Agent, or Firm—Blakely Sokoloff Taylor & Zafman LLP

(57) ABSTRACT

A product in the form of a segmented strip includes tabs to assist in dispensing individual segments from the strip. Segments of the strip are separated by lines of perforations running transverse to the strip. A tab of sufficient size to be easily grasped is adhesively secured to the strip across the line of perforations. The tab is positioned so that less than half of the area of the tab is disposed on the segment that is the first to be dispensed. The majority of the surface of the tab is disposed on a segment that will be subsequently dispensed. When the first segment is dispensed, the tab is retained on the next segment since the adhered surface on the next segment is greater. The exposed portion of the tab may then be readily located and grasped when the next segment is to be dispensed.

13 Claims, 2 Drawing Sheets

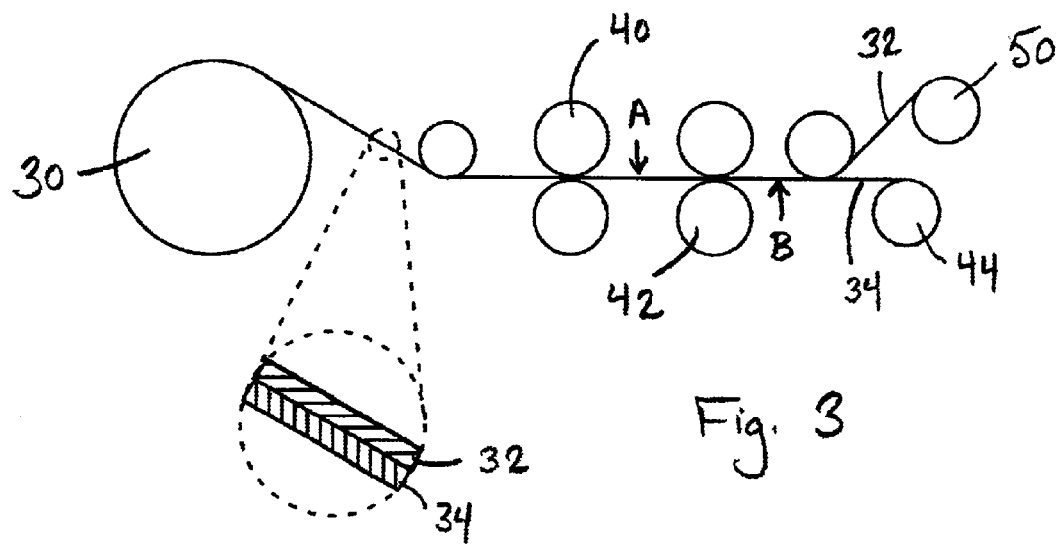
Fig. 3
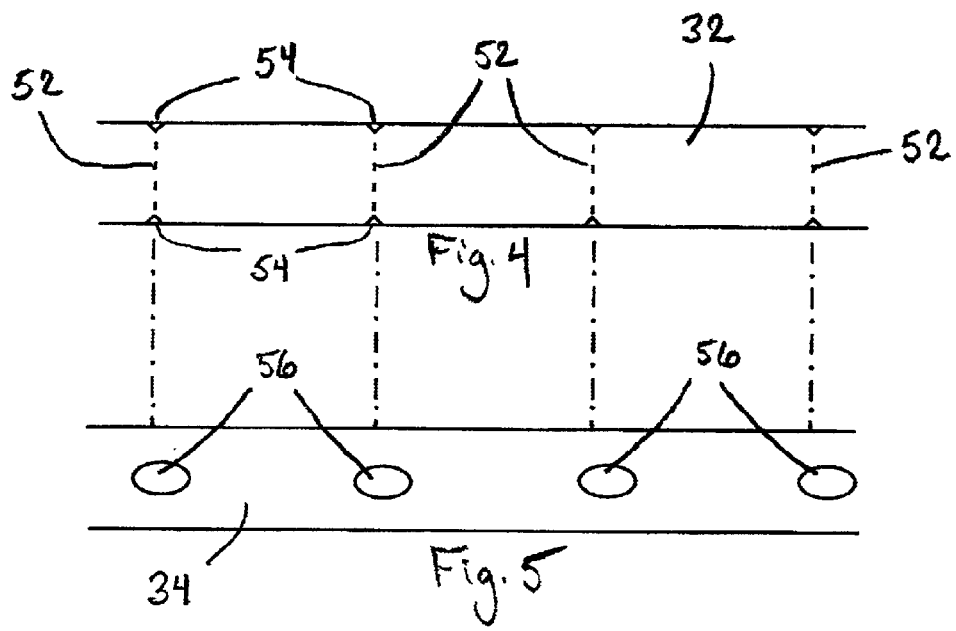
Fig. 4
Fig. 5

SEGMENTED PRODUCT WITH DISPENSING TABS

BACKGROUND OF THE INVENTION

1. Field of the Invention

This invention relates generally to the field of product packaging. More specifically, the invention relates to a pull-tab to assist in dispensing a product comprising a segment of an elongated strip, which may be packaged in a roll.

2. Background

Conventional self-adhesive bandages are typically packaged individually in a paper wrapper. Frequently, it is difficult to remove the bandage from the paper wrapper, remove the release liner from the adhesive and apply the bandage, especially in urgent care situations. A roll dispenser for self-adhesive bandages has been proposed to make the process of dispensing and applying a bandage more convenient. An example of such a dispenser is shown and described in U.S. Pat. No. 5,782,786.

A problem with adhesive bandages dispensed from a roll, which is a problem shared by many other products dispensed in a similar manner, is locating and grasping the end of the roll in order to dispense the next bandage. Typically, the consumer must feel around the circumference of the roll to locate the end of the roll and then lift the end with a fingernail. Various tab arrangements have been proposed in a context of other products to facilitate finding and lifting the end of a rolled adhesive product. Such arrangements are shown, for example, in U.S. Pat. Nos. 4,512,462; 4,727,616 and 6,014,788.

SUMMARY OF THE INVENTION

The present invention provides an improved tab to assist in dispensing a product from a segmented strip of such products. Segments of the strip are separated by lines of perforations running transverse to the strip. A tab of sufficient size to be easily grasped is adhesively secured to the strip across the line of perforations. The tab is positioned so that less than half of the area of the tab is disposed on the segment that is the first to be dispensed. The majority of the surface of the tab is disposed on a segment that will be subsequently dispensed. When the first segment is dispensed, the tab is retained on the next segment since the adhered surface on the next segment is greater. The exposed portion of the tab may then be readily located and grasped when the next segment is to be dispensed.

SUMMARY OF THE DRAWINGS

FIG. 3 diagrammatically illustrates a method of manufacturing a segmented product with tabs according to the present invention.

FIG. 4 is a plan view of the segmented product at location A in FIG. 3.

FIG. 5 is a plan view of the segmented product at location B in FIG. 3.

DETAILED DESCRIPTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Figure 1:
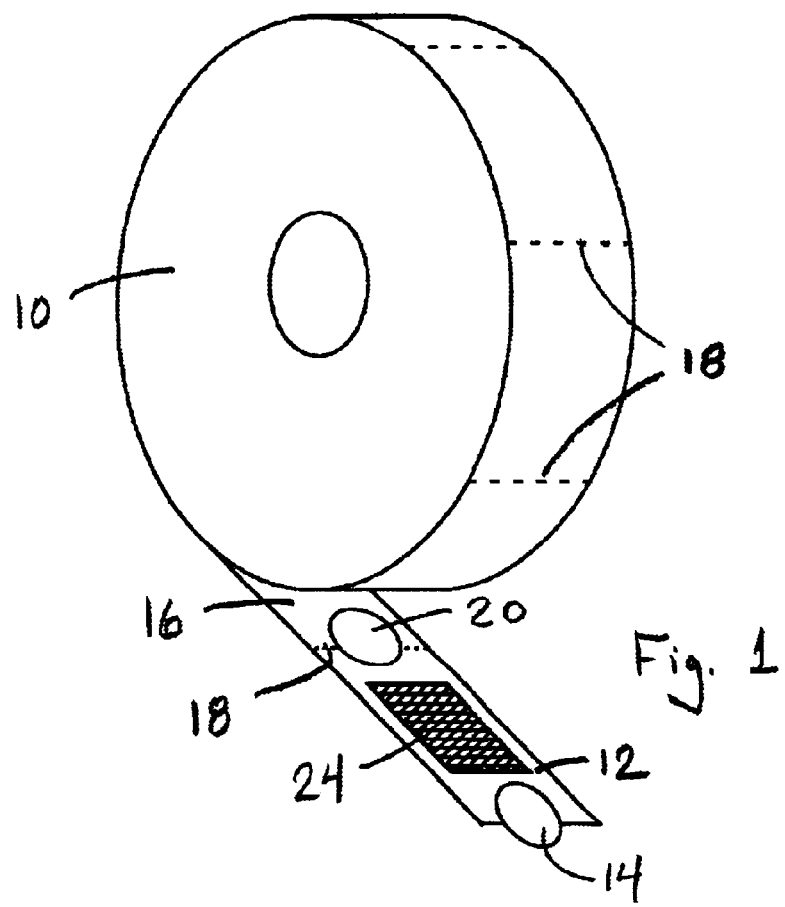
FIG. 1 is a perspective view of the present invention as used in conjunction with a roll of adhesive bandages.

FIG. 1 illustrates a roll 10 of adhesive bandages. Although the present invention is described in the context of an adhesive bandage product, it is to be understood that the invention may be applied to any product comprising segments of an elongated strip. Some examples of such products include adhesive tape, postage stamps, mailing labels, etc. As shown in FIG. 1, a first adhesive bandage 12 having an absorbent pad 24 has been partially detached from roll 10. This is facilitated by the use of tab 14. Bandage 12 is connected to a next bandage 16 on the roll. Bandages 12 and 16 are separated by a line of perforations 18. Tab 20 is adhesively secured to bandages 12 and 16 straddling the line of perforations. Less than half of the surface of tab 20 is disposed on bandage 12, whereas the majority of the surface of tab 20 is disposed on bandage 16. As bandage 12 is removed from roll 10 by separating at the line of perforations 18, tab 20 is retained on bandage 16 due to the fact that the surface area adhered to bandage 16 is greater than the surface area adhered to bandage 12. Once bandage 12 is removed, tab 20 will be exposed at the end of roll 10 to assist in dispensing bandage 16.

Figure 2:
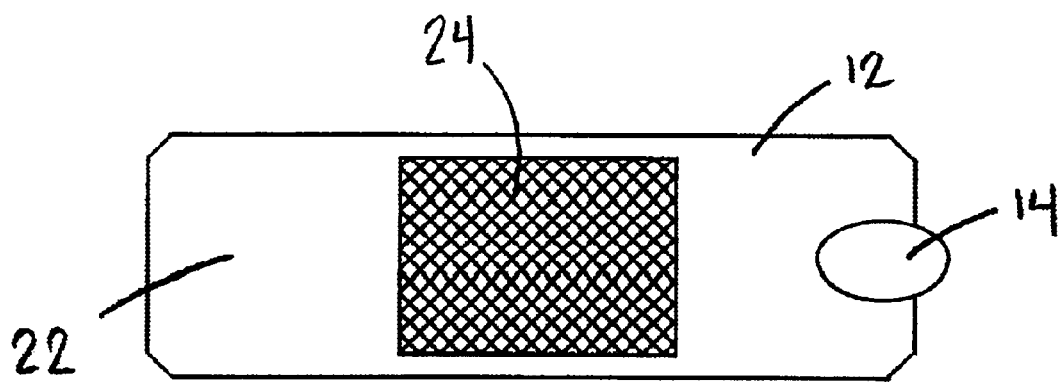
FIG. 2 is plan view of one of the adhesive bandages from the roll shown in FIG. 1.

FIG. 2 is a plan view of bandage 12 subsequent to its removal from roll 10. Bandage 12 is similar to a conventional adhesive bandage, having an adhesive surface 22 and an absorbent pad 24. Tab 14, which is secured to the adhesive surface of bandage 12 may be removed and discarded at the time the bandage is applied. If desired, the tab may be left in place to assist in removing the bandage from the skin.

FIG. 3 illustrates a method of manufacturing a segmented product with tabs in accordance with the present invention. Material for producing the segmented product is provided in bulk on roll 30. The material comprises a first material 32 having a second material 34 adhesively attached thereto. In the case of an adhesive bandage product, first material 32 would comprise the adhesive tape substrate for the bandage, which is typically a plastic film. Material 34, which will be processed to form the tabs of the present invention, is typically provided as a paper or plastic release liner for the adhesive surface of material 32.

Material drawn from roll 30 passes across cutter 40, which perforates the layer of material 32. The perforations do not extend into the layer of material 34. Next, cutter 42 die cuts the shape of the tabs into the layer of material 34. Here again, the depth of the cut is controlled so as not to extend into the layer of material 32. Cutters 40 and 42 are synchronized so that the tabs will be properly registered with the lines of perforations. After exiting cutter 42, the excess portion of the layer of material 34 is removed from material 32 and wound onto waste material take-up roll 44, leaving only the tabs adhered to material 32. The processed material is then wound onto take-up roll 50, which may constitute the final product or which may then be subjected to further processing. In the case of adhesive bandages, absorbent pads are applied to each segment of the processed material. This may be done at any convenient stage of the manufacturing process. Moreover, it should be noted that the sequence of cutting the perforations and the tabs is not critical. Hence, the tab cutting operation may be performed prior to the perforating operation, if desired.

FIG. 4 is a plan view of the layer of material 32 at location A in FIG. 3 after exiting cutter 40. Lines of perforations 52 extend transversely across the strip of material defining the product segments. Cutter 40 may also create notches 54 at the edges of the strip to further facilitate separation of the segments.

FIG. 5 is a plan view of the layer of material 34 at location B in FIG. 3 after exiting cutter 42. Tabs 56 have been die cut into the layer of material in registration with the lines of perforations 52. Tabs 56 may be round, oval, rectangular, or any other convenient shape. Only the tabs 56 remain on layer of material 32 after the excess of material 34 is removed (as shown in FIG. 3).

It will be recognized that the above-described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A segmented product comprising:
   a strip having a plurality of segments;
   a line of perforations transverse to the strip between adjacent segments;
   a tab having an area, the tab attached to the strip across the line of perforations with less than half of the area disposed on a first one of the adjacent segments and more than half of the area disposed on a second one of the adjacent segments;
   whereby, when said first one of the adjacent segments is detached from the strip, the tab remains attached to the second one of the adjacent segments to assist in subsequently detaching the second one of the adjacent segments from the strip.

2. The segmented product of claim 1 wherein the tab is adhesively attached to the strip.

3. The segmented product of claim 1 wherein the strip has a first side and a second side, and further comprising an adhesive coating on the first side, the tab being attached to the adhesive coating.

4. The segmented product of claim 1 wherein the strip is wound into a roll.

5. The segmented product of claim 1 wherein each of the plurality of segments comprises a bandage.

6. A method of making a segmented product comprising:
   providing an elongated strip of a first material having a second material adhesively attached to a first side of the first material;
   forming a plurality of lines of perforations in the first material transverse to the strip, thereby defining a plurality of segments;
   cutting the second material to form a tab straddling each of the lines of perforations, each tab having an area and being formed with less than half of the area on a first side of the corresponding line of perforations;
   removing the second material except for the plurality of tabs.

7. The method of claim 6 wherein the second material comprises a release liner.

8. The method of claim 6 wherein the first material comprises an adhesive tape.

9. The method of claim 8 further comprising attaching an absorbent pad to each segment of the first material.

10. The method of claim 9 wherein each of the plurality of segments comprises a bandage.

11. The method of claim 6 further comprising winding the elongated strip into a roll.

12. The method of claim 6 wherein the plurality of lines of perforations does not penetrate the second material.

13. The method of claim 6 wherein the tabs are formed without cutting the first material.

* * * * *